US011911621B2

(12) United States Patent
Ganty et al.

(10) Patent No.: US 11,911,621 B2
(45) Date of Patent: Feb. 27, 2024

(54) DEVICES AND SYSTEMS FOR ELECTRICAL STIMULATION AND METHODS OF USE

(71) Applicants: ONWARD MEDICAL N.V., Eindhoven (NL); ECOLE POLYTECHNIQUE FEDERALE DE LAUSANNE, Lausanne (CH)

(72) Inventors: Damien Ganty, Eindhoven (NL); Edoardo Paoles, Eindhoven (NL); Jocelyne Bloch, Paudex (CH); Gregoire Courtine, Lausanne (CH); Leonie Asboth, Lausanne (CH); Robin Demesmaeker, Morges (CH); Henri Lorach, Lausanne (CH); Jordan Squair, Lausanne (CH); Tomislav Milekovic, Fribourg (CH); Andreas Rowald, Lausanne (CH)

(73) Assignees: ONWARD MEDICAL N.V., Eindhoven (NL); ECOLE POLYTECHNIQUE FEDERALE DE LAUSANNE, Lausanne (CH)

( * ) Notice: Subject to any disclaimer, the term of this patent is extended or adjusted under 35 U.S.C. 154(b) by 345 days.

(21) Appl. No.: 17/357,836

(22) Filed: Jun. 24, 2021

(65) Prior Publication Data
US 2022/0409899 A1 Dec. 29, 2022

(51) Int. Cl.
*A61N 1/36* (2006.01)
*A61N 1/05* (2006.01)
*H01B 5/14* (2006.01)

(52) U.S. Cl.
CPC ....... *A61N 1/36062* (2017.08); *A61N 1/0553* (2013.01); *H01B 5/14* (2013.01)

(58) Field of Classification Search
CPC .......................... A61N 1/0553; A61N 1/36062
See application file for complete search history.

(56) References Cited

U.S. PATENT DOCUMENTS

| 8,108,051 B2 | 1/2012 | Cross, Jr. et al. |
| 2010/0070010 A1* | 3/2010 | Simpson .............. A61N 1/0553 607/148 |

(Continued)

FOREIGN PATENT DOCUMENTS

WO 2021021886 A1 2/2021

OTHER PUBLICATIONS

European Patent Office, Extended European Search Report Issued in Application No. 21181877.8, dated Jan. 10, 2022, Germany, 7 pages.

(Continued)

*Primary Examiner* — Alyssa M Alter
(74) *Attorney, Agent, or Firm* — McCoy Russell LLP (57) ABSTRACT

The present disclosure provides devices, systems, and methods for spinal cord stimulation. In some exemplary embodiments, a lead is provided. In one exemplary embodiment, the lead includes a paddle and an electrode array distributed in the paddle. The electrode array includes a first column of electrodes and a second column of electrodes. The first column of electrodes and the second column of electrodes are symmetric about the midline of the paddle. The first column of electrodes includes a first electrode, a second electrode, and a third electrode. The second column of electrodes includes a fourth electrode corresponding to the first electrode, a fifth electrode corresponding to the second electrode, and a sixth electrode corresponding to the third electrode. A vertical inter-electrode distance between the first electrode and the second electrode is larger than that between the second electrode and the third electrode.

11 Claims, 8 Drawing Sheets

(56) References Cited

U.S. PATENT DOCUMENTS

| | | | | |
|---|---|---|---|---|
| 2012/0016453 | A1* | 1/2012 | Feler | A61N 1/0553 607/148 |
| 2015/0005860 | A1 | 1/2015 | Howard et al. | |
| 2018/0093093 | A1* | 4/2018 | Courtine | A61B 5/24 |
| 2019/0224475 | A1 | 7/2019 | Dubuclet | |
| 2020/0155019 | A1* | 5/2020 | Esteller | A61N 1/36135 |

OTHER PUBLICATIONS

Lang, J. et al., "Über den lumbosakralen Teil des Durasackes und die Topographie seines Inhalts," Morphologia Medica, vol. 3, No. 1, May 1983, 21 pages. (Submitted with English Abstract).

Wagner, F. et al., "Targeted neurotechnology restores walking in humans with spinal cord injury," Nature, vol. 563, Nov. 1, 2018, 29 pages.

D'Avella, D. et al., "Microsurgical anatomy of lumbosacral spinal roots," Journal of Neurosurgery, vol. 51, No. 6, Dec. 1979, 5 pages.

Ko, H. et al., "Gross quantitative measurements of spinal cord segments in human," Spinal Cord, vol. 42, Jan. 9, 2004, 6 pages.

Zhou, M. et al., "Microsurgical Anatomy of Lumbosacral Nerve Rootlets for Highly Selective Rhizotomy in Chronic Spinal Cord Injury," The Anatomical Record: Advances in Integrative Anatomy and Evolutionary Biology, vol. 293, No. 12, Dec. 2010, 6 pages.

Schirmer, C. et al., "Heuristic map of myotomal innervation in humans using direct intraoperative nerve root stimulation," Journal of Neurosurgery—Spine, vol. 15, No. 1, Jul. 2011, 7 pages.

Capogrosso, M. et al., "A Computational Model for Epidural Electrical Stimulation of Spinal Sensorimotor Circuits," The Journal of Neuroscience, vol. 33, No. 49, Dec. 4, 2013, 15 pages.

Wenger, N. et al., "Closed-loop neuromodulation of spinal sensorimotor circuits controls refined locomotion after complete spinal cord injury," Science Translational Medicine, vol. 6, No. 255, Sep. 24, 2014, 11 pages.

Mamath, T. et al., "Morphology of Nerve Rootlets and Spinal Segments in the Lumbosacral Region: An Anatomical Study," Research Journal of Pharmaceutical, Biological and Chemical Sciences, vol. 7, No. 1, Jan. 14, 2016, 7 pages.

Lu, D. et al., "Engaging cervical spinal cord networks to re-enable volitional control of hand function in tetraplegic patients," Neurorehabilitation and Neural Repair, vol. 30, No. 10, Available Online May 18, 2016, Nov. 2016, 21 pages.

Frostell, A. et al., "A Review of the Segmental Diameter of the Healthy Human Spinal Cord," Frontiers in Neurology, vol. 7, No. 238, Dec. 23, 2016, 13 pages.

Mendez, A. et al., "Segment-specific orientation of the dorsal and ventral roots for precise therapeutic targeting of human spinal cord," Mayo Clinic Proceedings, vol. 96, No. 6, Feb. 2, 2020, 22 pages.

Chandrasekaran, S. et al., "Sensory restoration by epidural stimulation of the lateral spinal cord in upper-limb amputees," eLife, vol. 9, No. e54349, Jul. 21, 2020, 26 pages.

Toosi, A. et al., "Comparative neuroanatomy of the lumbosacral spinal cord of the rat, cat, pig, monkey, and human," Scientific Reports, vol. 11, No. 1, Jan. 21, 2021, 15 pages.

* cited by examiner

DEVICES AND SYSTEMS FOR ELECTRICAL STIMULATION AND METHODS OF USE

TECHNICAL FIELD

The present disclosure relates to systems and devices for electrical stimulation, and more particularly, to systems and devices for spinal cord stimulation and methods of use.

BACKGROUND

The spinal cord is an integral part of the central nervous system (CNS). Spinal cord injury (SCI), and other neurological disorders (e.g. stroke, Parkinson's disease, multiple sclerosis, autonomic failure, autonomic neuropathy or cancer of the neurological tissue which impair operation of descending sympathetic pathways that normally facilitate control of autonomic functions) can result in motor deficits. For instance, SCI interrupts the communication between the spinal cord and supraspinal centers, depriving these sensorimotor circuits from the excitatory and modulatory drives necessary to produce movement. Moreover, neurological disorders, such as SCI, can also cause sensory deficits and in autonomic dysfunctions. For example, SCI results in disconnection of some, most, or all descending sympathetic pathways that carry signals responsible for regulating arterial blood pressure, heart rate, bladder and/or bowel function, and/or breathing.

Epidural stimulation for spinal cord injury (SCI), also known as epidural electrical stimulation (EES) shows promising results for spinal cord injury therapy. The mechanisms are still unclear and under investigation, but EES can stimulate the leg muscles through the proprioceptive afferent fibers and restore the neuronal network in the spinal cord. EES system generally includes a pulse generator and one or more leads. The one or more leads are implanted and placed on top of the dura matter. A lead typically includes a lead body of insulative material that encloses wire conductors. The distal end of the lead includes an array of electrodes that are electrically coupled to the wire conductors. The proximal end of the lead body includes one or more terminals adapted to receive electrical pulses from the pulse generator. The one or more terminals are also electrically coupled to the wire conductors to deliver electrical pulses to the appropriate nerve tissue of the spinal cord via the electrodes.

Because of the complexity of the spinal cord, delivering EES using the lead to provide a therapy is quite challenging. Computational models were designed and tested on both rats and human (Capogrosso M, et al., A Computational Model for Epidural Electrical Stimulation of Spinal Sensorimotor Circuits, *Journal of Neuroscience*, 4 Dec. 2013, 33 (49)) to evaluate the neuronal and muscular response to the stimulation. Also, closed-loop neuromodulation systems that refined locomotion after complete spinal cord injury showed some therapeutic potential (Wenger N, et al., Closed-loop neuromodulation of spinal sensorimotor circuits controls refined locomotion after complete spinal cord injury, *Science Translational Medicine*, Sep. 24, 2014, 6(255)). However, currently available leads for spinal cord stimulation (SCS) were designed for chronic pain suppression and are inadequate for providing spinal cord injury therapies using EES.

SUMMARY

According to an exemplary embodiment of the present disclosure, a lead for spinal cord simulation is provided. In some embodiments, the lead includes a paddle and an electrode array distributed in the paddle. In some embodiments, the electrode array includes a first column of electrodes and a second column of electrodes. In some embodiments, the first column of electrodes and the second column of electrodes are symmetric about the midline of the paddle. In some embodiments, the first column of electrodes includes a first electrode, a second electrode, and a third electrode. In some embodiments, the second column of electrodes includes a fourth electrode corresponding to the first electrode, a fifth electrode corresponding to the second electrode, and a sixth electrode corresponding to the third electrode. In some embodiments, a vertical inter-electrode distance between the first electrode and the second electrode is larger than that between the second electrode and the third electrode.

According to an exemplary embodiment of the present disclosure, a method of providing therapy for neurological disorders is provided. In some embodiments, the method includes providing epidural electrical stimulation of the dura mater of at least one dorsal root of one or more spinal segments using a lead. In some embodiments, the method further includes placing the lead on top of the dura matter of the spinal cord such that the electrodes of the first column and the second column are positioned at the dorsal root entry zone of the one or more spinal segments. In some embodiments, the method further includes treating a neuromotor disorder or an autonomic dysfunction. In some embodiments, the lead includes a paddle and an electrode array distributed in the paddle. In some embodiments, the electrode array includes a first column of electrodes and a second column of electrodes. In some embodiments, the first column of electrodes and the second column of electrodes are symmetric about the midline of the paddle. In some embodiments, the first column of electrodes includes a first electrode, a second electrode, and a third electrode. In some embodiments, the second column of electrodes includes a fourth electrode corresponding to the first electrode, a fifth electrode corresponding to the second electrode, and a sixth electrode corresponding to the third electrode. In some embodiments, a vertical inter-electrode distance between the first electrode and the second electrode is larger than that between the second electrode and the third electrode.

According to an exemplary embodiment of the present disclosure, a system for spinal cord stimulation is provided. In some embodiments, the system includes a pulse generator and a lead. In some embodiments, the lead includes a paddle and an electrode array distributed in the paddle. In some embodiments, the electrode array includes a first column of electrodes and a second column of electrodes. In some embodiments, the first column of electrodes and the second column of electrodes are symmetric about the midline of the paddle. In some embodiments, the first column of electrodes includes a first electrode, a second electrode, and a third electrode. In some embodiments, the second column of electrodes includes a fourth electrode corresponding to the first electrode, a fifth electrode corresponding to the second electrode, and a sixth electrode corresponding to the third electrode. In some embodiments, a vertical inter-electrode distance between the first electrode and the second electrode is larger than that between the second electrode and the third electrode. In some embodiments, the lead includes two lead bodies configured to electrically couple the electrodes of the electrode array to the pulse generator.

Additional disclosure of the disclosed embodiments will be set forth in part in the description that follows.

It is to be understood that both the foregoing general description and the following detailed description are examples and explanatory only and are not restrictive of the disclosed embodiments as claimed.

BRIEF DESCRIPTION OF THE DRAWINGS

The accompanying drawings, which comprise a part of this specification, illustrate several embodiments and, together with the description, serve to explain the principles and features of the disclosed embodiments. In the drawings.

DETAILED DESCRIPTION

Reference will now be made in detail to exemplary embodiments. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the devices, systems, methods, and examples are illustrative only and are not intended to be necessarily limiting.

Disclosed embodiments provide devices, systems, and methods for providing EES of the spinal cord. In some embodiments, devices, systems, and methods for providing therapies to treat spinal cord injury using EES are provided.

Figure 1:
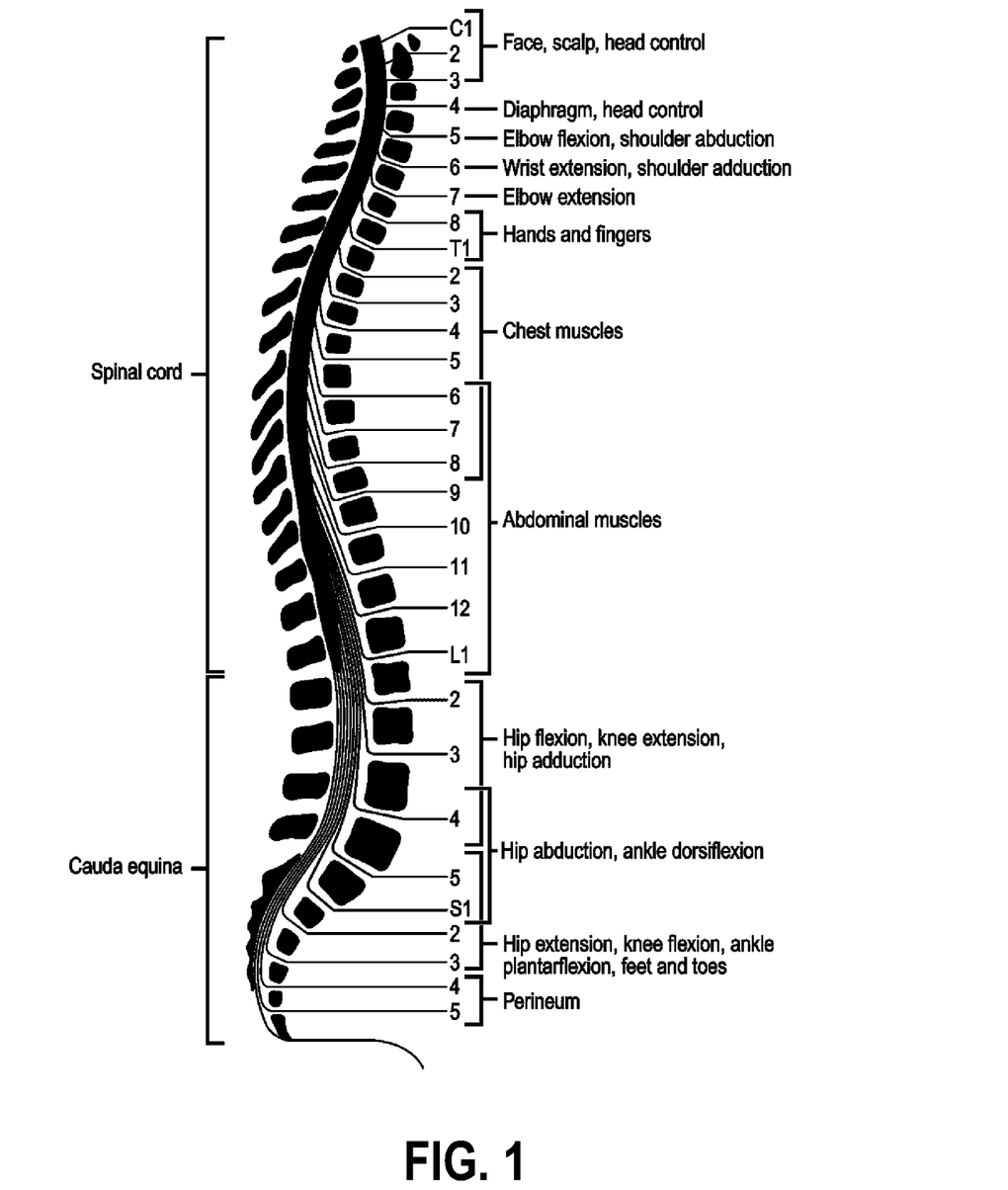
FIG. 1 illustrates the human spinal cord and spinal nerves with their main functions.

FIG. 1 illustrates the human spinal cord and spinal nerves with their main functions. The spinal cord is a long, thin, tubular structure made up of nervous tissue, which extends from the medulla oblongata in the brainstem to the lumbar region of the vertebral column. At the end of the spinal cord, the cord fibers separate into the cauda equina and continue to travel through the vertebral column to the coccyx.

At each level of the spinal cord, efferent spinal nerve fibers, i.e., the axons of motor neurons, exit the spinal cord via the ventral roots, and afferent spinal nerve fibers, i.e., the axons of sensory neurons, enter the spinal cord via the dorsal roots. A spinal nerve is a mixed nerve comprising an efference nerve fiber from the ventral root and an afferent nerve fiber from dorsal root. A spinal nerve carries motor, sensory, and autonomic signals between the spinal cord and the body. Spinal cord injury often damages or severs the axons and reduces or cuts the flow of sensory information and commands between the brain and the body.

In the human body there are 31 pairs of spinal nerves, one on each side of the vertebral column. These pairs of spinal nerves are grouped into the corresponding cervical (C), thoracic (T), lumbar (L), sacral (S), and coccygeal regions of the spine. The spinal nerves are numbered according to the vertebrae segment above which it exits the spinal canal. There are eight pairs of cervical nerves (C1-C8), twelve pairs of thoracic nerves (T1-T12), five pairs of lumbar nerves (L1-L5), five pairs of sacral nerves (S1-S2), and one pair of coccygeal nerves.

Different groups of spinal nerves innervate different areas of the human body. For example, as shown in FIG. 1, the cervical nerves innervate the muscles and provide sensation for the head, neck, and diaphragm, as well as the upper limbs; the thoracic nerves innervate the muscles and provide sensation for organs and glands in the chest and abdomen; the lumbar nerves innervate the muscles and provide sensation for the abdomen, hip, knee, and ankle; and the sacral nerves innervate the muscles and provide sensation for the pelvis and lower limb. In addition, the cauda equina extends to sensory innervation of the perineum and, partially, parasympathetic innervation of the bladder.

It is recognized that EES of the dura mater of the dorsal spinal roots below the level of injury could facilitate the recovery of some volitional motoric functions and autonomic functions previously lost due to spinal cord injury. Moreover, EES applied to the dura mater of the dorsal roots of a spinal region facilitates restoration of functions of a targeted area of the body innervated by the dorsal roots of that spinal region. For example, EES applied at one or more locations at C4-T1 may provide a therapy for restoring voluntary motion of upper limbs; EES applied at one or more locations at T10-T12 may provide a therapy for restoring blood pressure regulation and trunk stability; EES applied at one or more locations at L1-S1 or T12-S1 may provide a therapy for restoring voluntary motion; EES applied at one or more locations at L5-S3 or L5-S4 may provide a therapy for restoring certain autonomic functions, such as bladder control.

Figure 2:
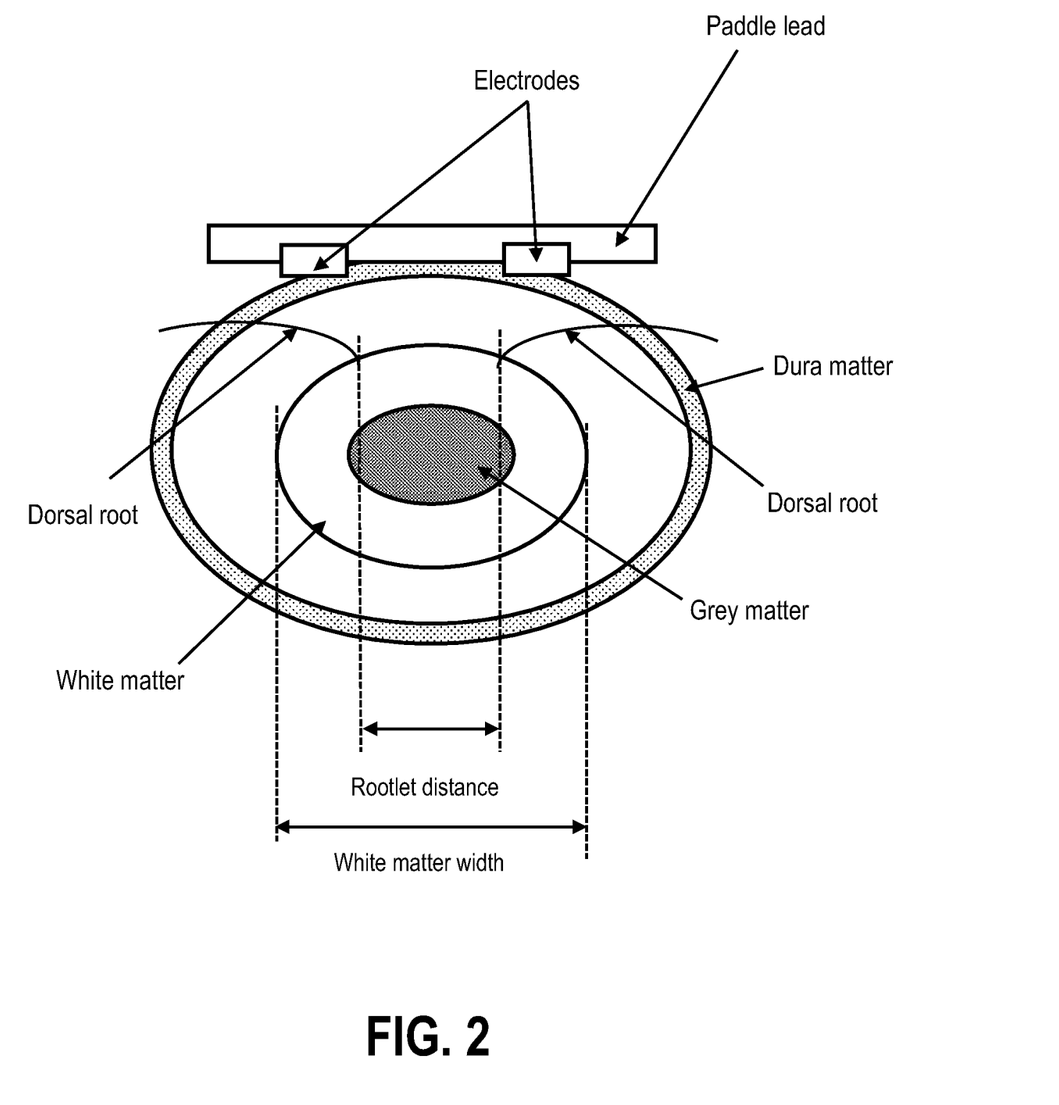
FIG. 2 depicts a simplified cross section of the spinal cord showing exemplary positions of electrodes at the dorsal root entry zone, according to some embodiments of the present disclosure.

Dorsal root fans out into dorsal rootlets before entering the spinal cord. Selective recruitment of the neural fibers in the dorsal roots can be achieved by positioning the electrodes above the locations where dorsal roots or dorsal rootlets enter the spinal cord, i.e., at the dorsal root entry zone. FIG. 2 depicts a simplified cross section of the spinal cord showing exemplary positions of electrodes over the spinal cord for providing EES, according to some embodiments of the present disclosure. As shown in FIG. 2, selective recruitment of dorsal root axons can be achieved by electrodes positioned over the root entry zone. Such positioning allows the selective recruitment of the neural fibers in the dorsal roots while avoiding or reducing the non-desired recruitment of the somatosensory fibers extending within the dorsal columns.

Commercially available leads for spinal cord stimulation were designed for treating chronic pain and typically apply stimulation over the midline of the spinal cord. These leads are inadequate for recruitment of spinal dorsal roots and not suitable for EES. Thus, leads specifically targeting spinal dorsal roots are desired. Furthermore, lead paddles of sufficient lengths to have electrodes covering one or more spinal cord segments innervating one or more targeted areas for restoring desired functions, certain motoric or autonomic functions, such as blood pressure or bladder control, are desired. EES provided at locations away from the dorsal root entry zones and/or away from the spinal cord segments innervating the targeted areas may require more electrical current and may trigger adverse muscle contractions. Therefore, leads that effectively recruit dorsal roots and cover all targeted spinal cord segments are desired. Such leads for EES would provide the same therapeutic effect with substantially lower stimulation currents and would reduce the adverse recruitment of dorsal spinal fibers.

According to one aspect of the present disclosure, leads for EES are provided. In some embodiments, the leads are designed based on anatomical measurements of the spinal cord and computational simulations that identify electrode locations that maximize the recruitment of the dorsal roots innervating one or more spinal cord segments. In some embodiments, the one or more spinal cord segments are selected based on the functions desired to restore. For example, a lead may have a distribution of electrodes that maximizes the recruitment of the dorsal roots innervating the final three thoracic spinal segments to cover all hemodynamic hotspots to restore blood pressure regulation.

Figure 3:
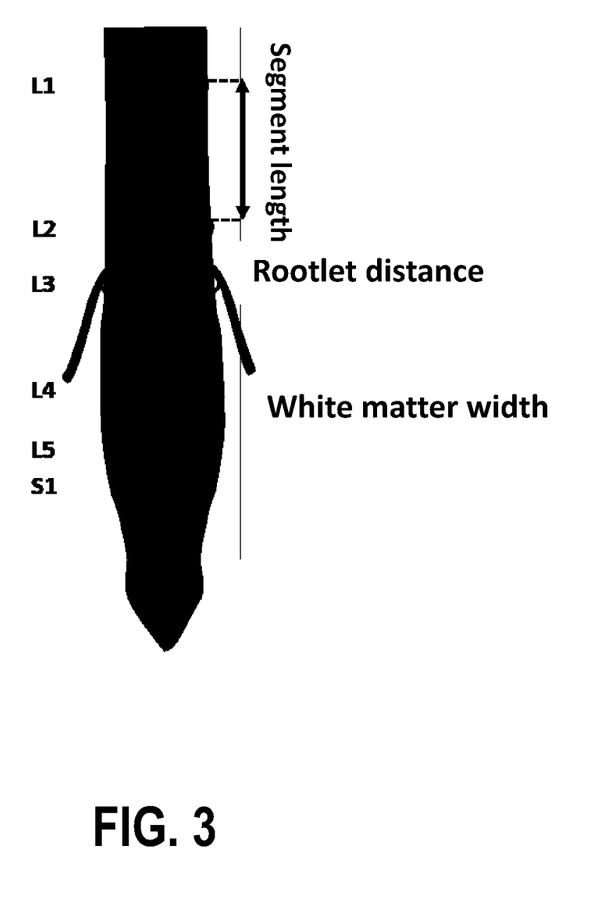
FIG. 3 illustrates exemplary anatomical landmarks of spinal cord measurements, according to some embodiments of the present disclosure.

In some embodiments, leads are designed based on one or more exemplary anatomical landmarks of the spinal cord measurements. FIG. 3 illustrates three exemplary anatomical landmarks of spinal cord measurements: the segment length, rootlet distance, and white matter width. Measurement data of these anatomical landmarks of the cervical, thoracic, lumbar, and sacral regions of the spinal cord were collected from a study of 12 cadavers ("cadaver study"), magnetic resonance imaging data of 11 healthy volunteers ("MR imaging data"), and data reported in literature references. The literature references are discussed below in the examples described with reference to FIGS. 4-8.

In some embodiments, distribution and/or locations of electrodes of a lead can be determined based on the collected measurement data. Because of the complexity of the spinal cord, the anatomical measurements vary for different spinal cord segments and for different individuals. Thus, the distribution and/or locations of electrodes of leads for EES of different spinal cord segments can be different. In some embodiments, the distribution and/or locations of electrodes of a lead are adjusted to mitigate interpatient variability and cover a larger patient population. In some embodiments, a spinal cord model is generated based on the collected measurement data.

In some embodiments, computational simulations using the spinal cord model are performed to evaluate the performance, such as selectivity and effectiveness, of stimulation at different locations of the electrodes for recruiting the dorsal roots. In some embodiments, computational simulations are performed using the Multiphysics platform Sim4Life (www.zmt.swiss/sim4life/). In some embodiments, the computational simulations are coupled electromagnetic-neuronal dynamics simulations to evaluate the performance of electrodes positioned at different locations over the spinal cord in-silico. In some embodiments, the distribution and/or locations of electrodes of a lead are adjusted to increase selectivity and effectiveness of EES at the dorsal roots and/or reduce adverse effects, such as adverse muscle contractions or undesired stimulation of contralateral roots. As a non-limiting example, the location of an electrode of a lead may be designed to be horizontally offset from a location for stimulating a left dorsal root (or a right dorsal root) with the highest selectivity to reduce undesired stimulation of corresponding right dorsal roots (or left dorsal roots), to account for errors during implantation of the lead, and/or to account for migration of the lead after implantation.

As a non-limiting example, based on computational simulations, it was found that an electrode has the highest unipolar selectivity when it is positioned in the middle of the target spinal segment along the longitudinal axis. Further, when an electrode is positioned closer to the midline of the spinal cord, its selectivity decreases due to unwanted stimulation of contralateral roots. As used herein, a midline of the spinal cord refers to the median line of bilateral symmetry of the spinal cord and extends along the longitudinal or rostro-caudal axis.

As another non-limiting example, based on computational simulations, it was found that bipolar stimulation with an anode placed horizontally to the cathode is not effective in stimulating nerve fibers because it generates an electrical field that is perpendicular to the nerve fibers. Further, bipolar selectivity can be increased when the anode is placed diagonally to the cathode along the trajectory of the nerve fibers. The effectiveness of bipolar stimulation can decrease when the anode is placed further away from the cathode. In some embodiments, the distance between a pair of cathode and anode for providing bipolar stimulation does not exceed about the distance of half of an electrode.

In some embodiments, a lead for EES includes a paddle, a plurality of electrodes, and a pair of lead bodies. In some embodiments, the lead bodies are connected to the paddle at their distal ends and connected to a pulse generator at their proximal ends. In some embodiments, the lead bodies each enclose a wire conductor connecting the electrodes and the pulse generator. Each of the plurality of electrodes is electrically coupled to the wire conductor of one of the lead bodies, e.g., via an electric wire, to receive electrical pulses from the pulse generator. In some embodiments, the paddle and/or lead bodies are made of a suitable physiologically inert and electrically insulating material, such as silicone rubber or polyethylene.

In some embodiments, the paddle of a lead has an elongated rectangular shape having a longitudinal axis and a horizontal axis. The longitudinal axis is to align or substantially align with the longitudinal or rostro-caudal axis of the spinal cord after the paddle is surgically implanted. The horizontal axis is perpendicular to the longitudinal axis. In some embodiments, the rectangular shape of the paddle has rounded corners. In some embodiments, the paddle of a lead includes a first paddle portion and a second paddle portion. The first paddle portion includes a plurality of cavities configured to receive the plurality of electrodes within. The second paddle portion includes a plurality of apertures to accept electrodes, allowing top surfaces of the electrodes to extend slightly beyond the paddle to provide electrical contact with the tissue to be stimulated. In some embodiments, the top surfaces of the electrode are to be exposed on the ventral side of the paddle after the paddle is surgically implanted.

As used herein, a midline of a paddle refers to the median line of bilateral symmetry of the paddle and extends longitudinally. In some embodiments, the plurality of electrodes of the lead are distributed symmetrically about the midline of the paddle. As used herein, a column of electrodes refers to a plurality of electrodes distributed across the paddle along the longitudinal axis. In some embodiments, a lead includes a plurality of columns of electrodes. In some embodiments, a lead includes a first column of electrodes and a second column of electrodes. The first column of electrodes and the second column of electrodes are symmetric about the midline of the paddle. Description of the first column of electrodes is equally applicable to the second column of electrodes. As described herein, the number of electrodes in each column may change based on the desired density of electrodes on the lateral sides of the paddle and the available stimulation channels of the pulse generator.

As defined herein, an inter-electrode distance refers to the edge-to-edge distance between two adjacent electrodes. A vertical inter-electrode distance refers to the vertical distance between the bottom edge of a first electrode and a top edge of a second electrode located vertically below and adjacent to the first electrode. A horizontal inter-electrode distance refers to the horizontal distance between the left edge of a first electrode and the right edge of a second electrode located to the right of and adjacent to the first electrode. Alternatively, a horizontal interelectrode distance refers to the horizontal distance between the right edge of a first electrode and the left edge of a second electrode located to the left of and adjacent to the first electrode.

In some embodiments, the vertical inter-electrode distances of the first column of electrodes are determined based on the lengths of the spinal segments to be covered by the electrodes. In some embodiments, the vertical inter-electrode distances of the first column of electrodes are substantially the same across the length of the paddle. In some embodiments, the vertical inter-electrode distances of the first column of electrodes vary. Anatomical measurements indicate that in certain spinal regions, the segment length (see FIG. 3) decreases rostro-caudally over one or more spinal segments. In some embodiments, the vertical inter-electrode distance of the first column of electrodes decreases to follow the decreasing segment length, thereby increasing selective recruitment of spinal dorsal roots.

In some embodiments, the horizontal inter-electrode distances between electrodes of the first column and electrodes of the second column are determined based on the rootlet distances of the spinal segments to be covered by the electrodes. In some embodiments, the horizontal inter-electrode distances between electrodes of the first column and electrodes of the second column are substantially the same across the length of the paddle. In some embodiments, the horizontal inter-electrode distances between electrodes of the first column and electrodes of the second column vary. Anatomical measurements indicate that in certain spinal regions, the rootlet distance (see FIG. 3) decreases over one or more spinal segments. In some embodiments, the horizontal inter-electrode distance between electrodes of the first column and electrodes of the second column decreases to follow the decreasing rootlet distance, thereby increasing selective recruitment of spinal dorsal roots.

In some embodiments, a lead includes a third column of electrodes distributed along the midline of the paddle. In some embodiments, the third column of electrodes may be used for shielding unwanted stimulation of contralateral roots. In some embodiments, the third column of electrodes may be used for performing multipolar stimulation. In some embodiments, the third column of electrodes may be used for mitigating the risk of misalignment of the paddle on the spinal cord. In some embodiments, the vertical inter-electrode distances of the third column of electrodes are substantially the same. In some embodiments, the vertical inter-electrode distances of the third column of electrodes vary. In some embodiments, the inter-electrode distance of the third column of electrodes decreases to follow the decreasing segment lengths of a spinal region, thereby increasing selective recruitment of spinal dorsal roots.

Exemplary leads for providing EES of the cervical, thoracic, lumbar, and sacral spinal regions are described below with references to FIGS. 4-8.

Exemplary Leads for Stimulating the Cervical Spinal Region

Anatomical measurement data of the segments of interest C4-T1 were collected from MR imaging data (see Table 1) and literature references. The literature references include Lu D C, et al., Engaging Cervical Spinal Cord Networks to Reenable Volitional Control of Hand Function in Tetraplegic Patients, *Neurorehabilitation and Neural Repair*, November, 2016, 30(10):951-962; Chandrasekaran, et al., Sensory restoration by epidural stimulation of the lateral spinal cord in upper-limb amputees, eLife, July 2020, 9:e54349, and Schirmer et al., Heuristic map of myotomal innervation in humans using direct intraoperative nerve root stimulation, *Journal of Neurosurgery: Spine SPI*, July, 2011, 15(1), 64-70. All of these references are incorporated herein by reference in their entireties.

TABLE 1

Average measurements of anatomical landmarks of selected cervical segments from MR imaging data.

| Segment | Segment length (distance between the centers of two vertebrae $C_i$ and $C_{i+1}$) (mm) | Diameter (maximum diameter of the spinal cord at the level of the center of the vertebra $C_i$) (mm) | Segment length (the distance between the roots of two vertebrae $C_i$ and $C_{i+1}$) (mm) |
| --- | --- | --- | --- |
| C2 | 19.86 | 10.50 | 16.60 |
| C3 | 15.19 | 10.21 | 17.76 |
| C4 | 15.14 | 10.92 | 17.07 |
| C5 | 15.07 | 11.71 | 17.04 |
| C6 | 15.13 | 12.13 | 16.63 |
| C7 | 16.00 | 11.38 | 16.53 |
| C8 |  | 11.04 | 16.06 |

Figure 4:
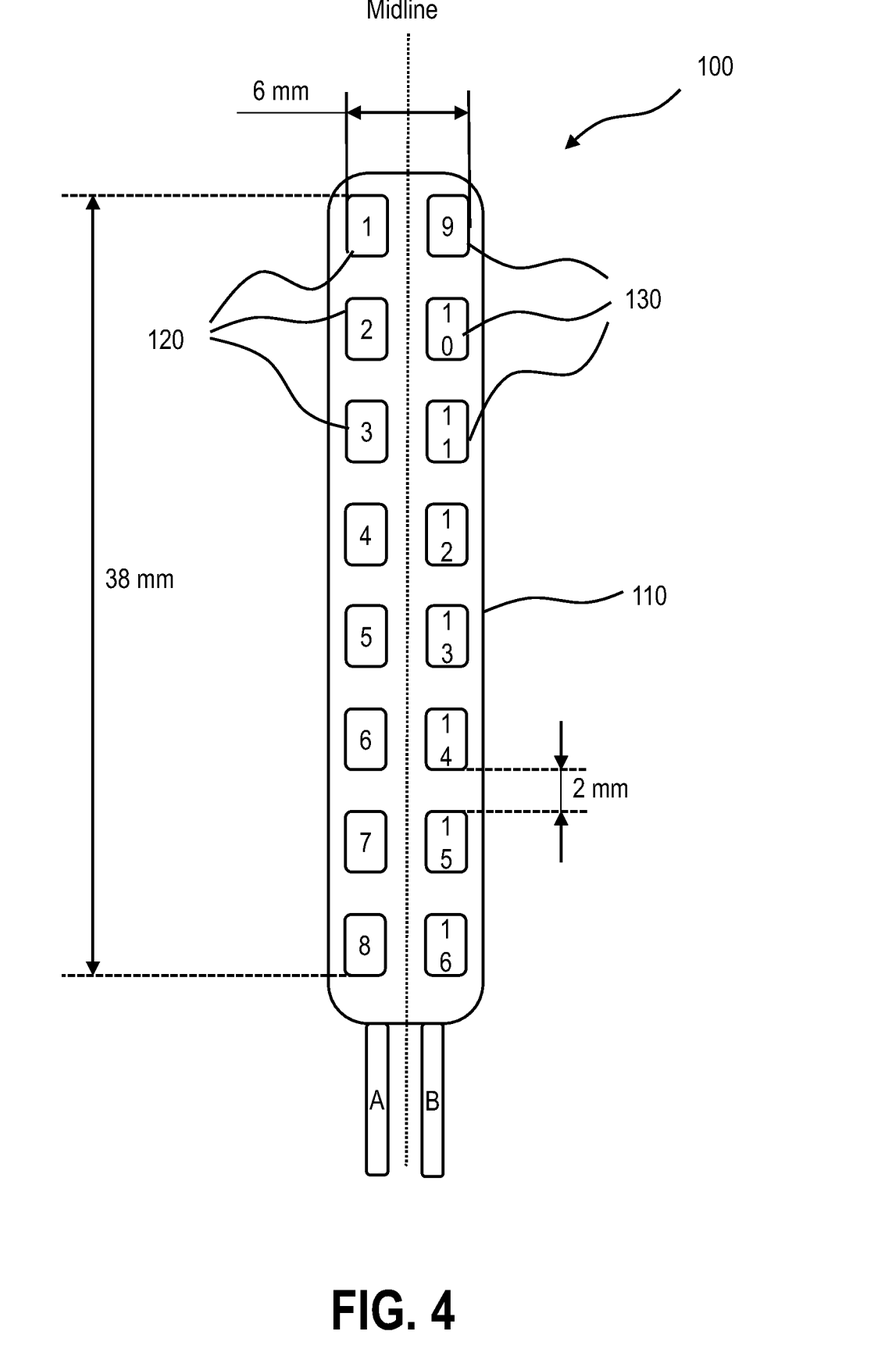
FIG. 4 depicts an exemplary lead for stimulating the cervical spinal region, according to some embodiments of the present disclosure.

In some embodiments, based on the collected anatomical measurements and subsequent computational simulations, a lead for providing EES of selected segments in the cervical region is provided. FIG. 4 depicts an exemplary lead 100 for stimulating the cervical spinal region, according to some embodiments of the present disclosure. In some embodiments, lead 100 includes a paddle 110 and a plurality of electrodes 120 of a first column and a plurality of electrodes 130 of a second column.

For example, as shown in FIG. 4, in some embodiments, lead 100 includes an array of 16 electrodes symmetrically distributed about the midline of the paddle. The 16 electrodes are numbered and distributed in two columns, each column comprising 8 electrodes. In some embodiments, the 16 electrodes are identical. In some embodiments, the electrodes have a rectangular shape. In some embodiments, the size of an electrode 120 or 130 is about 3.0 mm by about 2.0 mm. In some embodiments, lead 100 includes a lead body A and a lead body B. Lead body A contain conductors contacts from the first column of electrodes, e.g., electrodes 1-8, and lead body B contain conductors contacts from the second column of electrodes, e.g., electrodes 9-16.

In some embodiments, the width of the paddle is equal to or less than about 9.0 mm. In some embodiments, the thickness of the paddle is equal to or less than about 2.5 mm. In some embodiments, as shown in FIG. 4, the distance between the top edge of electrode 1 and the bottom edge of electrode 8 along the longitudinal axis is from about 35.0 mm to about 85.0 mm, such as from about 35.0 mm to about 65.0 mm. In some embodiments, the vertical inter-electrode distance of the first column of electrodes 120 or the second column of electrodes 130 (e.g., the distance between the bottom edge of electrode 14 and the top edge of electrode 15) is from about 1.5 mm to about 3.0 mm, such as about 2.0 mm. In some embodiments, the horizontal inter-electrode distance between an electrode 120 of the first column and an electrode 130 of the second column (e.g., the distance between the left edge of electrode 1 and the right edge of electrode 9) is from about 5.0 mm to about 7.0 mm, such as about 6.0 mm.

As described herein, actual dimensions of the paddle and the actual sizes and/or inter-electrode distances of the electrodes consistent with the present disclosure may deviate from the exemplary ranges described herein due to accommodations and/or errors that occur during manufacturing, for example. In some embodiments, such deviations can range from about 0.1 mm to about 0.2 mm.

In some embodiments, more than one leads 100 are used for providing EES to the cervical region. For example, the longitudinal span of the electrodes of lead 100 of FIG. 4 is about 38.0 mm. Two leads 100 of FIG. 4 may be used in serial, e.g., one above the other or one after the other along the longitudinal axis, to provide longer coverage, such as about 8 cm, over the cervical region of the spinal cord. In some embodiments, two leads 100 of FIG. 4 may be used in parallel, one next to the other on one lateral side (left or right) to provide wider coverage, such as about 12.0 mm, over the cervical region of the spinal cord.

Exemplary Leads for Stimulating the Thoracic Spinal Region

Anatomical measurement data on the segments of interest T10-T12 along the spinal cord were collected from the cadaver study, MR imaging data, and/or literature references (see Tables 2-3). The literature references include Ko et al., Gross quantitative measurements of spinal cord segments in human. *Spinal Cord* 42, 35-40 (2004); Frostell et al., A Review of the Segmental Diameter of the Healthy Human Spinal Cord. *Front Neurol.*, December 2016, 7:238; Mendez et al., Segment-Specific Orientation of the Dorsal and Ventral Roots for Precise Therapeutic Targeting of Human Spinal Cord. *Mayo Clin Proc.* June 2021, 96(6):1426-1437. All of these references are incorporated herein by reference in their entireties.

TABLE 2

Average measurements of selected thoracic segment lengths from cadaver study, MR imaging data, and literature.

| Segment | Cadaver (mm) | MR imaging data (mm) | Ko 2004 (mm) | Mendez 2020 (mm) |
|---|---|---|---|---|
| T10 | 16.87* | 19.88* | 16.23 | 25.29 |
| T11 | 15.43* | 18.2* | 13.87 | 22.38 |
| T12 | 14 | 16.5 | 12.37 | 18.48 |
| Total | 46.3 | 54.58 | 42.48 | 66.16 |

*These average measurements are estimations based on reports from Frostell 2016.

TABLE 3

Average measurements of white matter widths and rootlet distances of selected thoracic segments from Mendez 2020.

| Segment | Average white matter diameter (mm) | Average rootlet distance (mm) |
|---|---|---|
| T10 | 7.55 | 5.46 |
| T11 | 7.99 | 5.46 |
| T12 | 8.22 | 5.95 |

Figure 5:
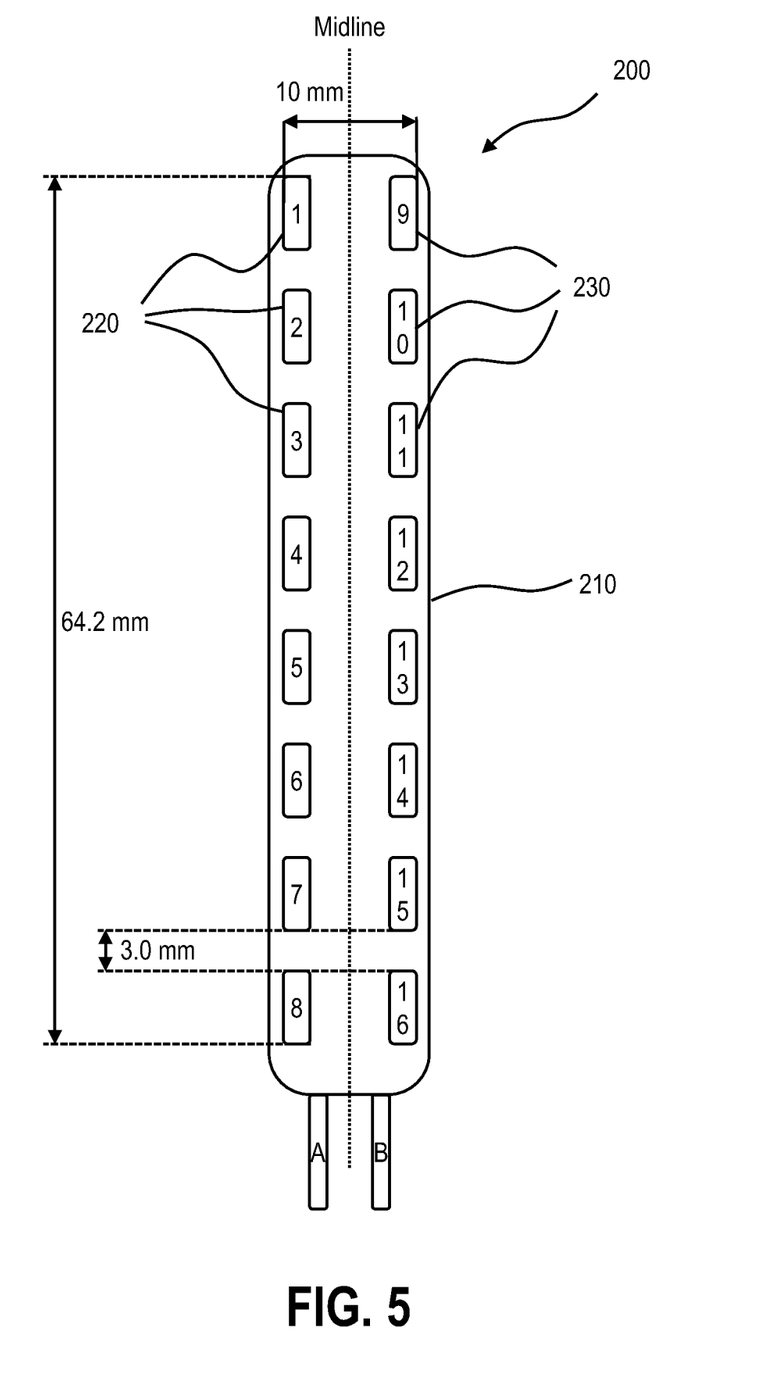
FIG. 5 depicts an exemplary lead for stimulating the thoracic spinal region, according to some embodiments of the present disclosure.

In some embodiments, based on the collected anatomical measurements and subsequent computational simulations, a lead for providing EES of selected segments in the thoracic region is provided. FIG. 5 depicts an exemplary lead 200 for stimulating the thoracic spinal region, according to some embodiments of the present disclosure. In some embodiments, lead 200 includes a paddle 210 and a plurality of electrodes 220 of a first column and a plurality of electrodes 230 of a second column. For example, as shown in FIG. 5, in some embodiments, lead 200 includes an array of 16 electrodes symmetrically distributed about the midline of the paddle. The 16 electrodes are numbered and distributed in two columns, each column comprising 8 electrodes. In some embodiments, the 16 electrodes are identical. In some embodiments, the electrodes have a rectangular shape. In some embodiments, the size of an electrode 220 or 230 is about 5.4 mm by 2.04 mm. In some embodiments, lead 200 includes a lead body A and a lead body B. Lead body A contain conductors contacts from the first column of electrodes, e.g., electrodes 1-8, and lead body B contain conductors contacts from the second column of electrodes, e.g., electrodes 9-16.

In some embodiments, the width of the paddle of lead 200 is equal to or less than about 13.0 mm. In some embodiments, the thickness of the paddle is equal to or less than about 2.5 mm. In some embodiments, as shown in FIG. 5, the distance between the top edge of electrode 1 and the bottom edge of electrode 8 along the longitudinal axis is from about 57.0 mm to about 71.0 mm, such as about 64.2 mm.

In some embodiments, the vertical inter-electrode distance of the first column of electrodes 220 or the second column of electrodes 230 (e.g., the distance between the bottom edge of electrode 7 and the top edge of electrode 8) is from about 2.0 mm to about 4.0 mm, such as about 3.0 mm. In some embodiments, the horizontal inter-electrode distance between an electrode 220 of the first column and an electrode 230 of the second column (e.g., the distance between the left edge of electrode 1 and the right edge of electrode 9) is from about 8.0 mm to about 12.0 mm, such as about 10.0 mm. In some embodiments, the center of electrode 220 or electrode 230 is about 3.0 mm to about 5.0 mm, such as about 4.0 mm, away from the midline of paddle 210.

In some embodiments, lead 200 is used for providing a therapy for restoring blood pressure regulation using EES. For example, electrodes of lead 200 can be placed at the hemodynamic hotspots located above the dorsal root entry zones of the final three thoracic spinal segments after surgical implantation. Such placement of the electrodes of lead 200 may achieve maximum recruitment of sympathetic spinal circuits that control the systemic blood pressure through contraction of arteries. See Squair et al. Neuroprosthetic baroreflex controls haemodynamics after spinal cord injury. *Nature* 590, 308-314 (2021), which is incorporated herein by reference in its entirety.

Exemplary Leads for Stimulating the Lumbar Spinal Region

Anatomical measurement data on the segments of interest L1-S1 along the spinal cord were collected from the cadaver study, MR imaging data, and/or literature references (see Tables 4-6). The literature references include Ko 2004; Frostell 2016; Mendez 2021; Lang et al., Uber den lumbo-sakralen Teil des Duralsackes und die Topographie seines Inhalts, *Morphol. Med.*, 3:2746 (1983); Toossi et al. Comparative neuroanatomy of the lumbosacral spinal cord of the rat, cat, pig, monkey, and human. *Sci Rep* 11, 1955 (2021); Zhou et al., Microsurgical anatomy of lumbosacral nerve rootlets for highly selective rhizotomy in chronic spinal cord injury, *The Anatomical Record*, 293:2123-2128 (2010); and d'Avella et al., Microsurgical anatomy of lumbosacral spinal roots. *J Neurosurg.* 51(6):819-23 (December 1979). All of these references are incorporated herein by reference in their entireties.

TABLE 4

Average measurements of selected lumbar and sacral segment lengths from cadaver study, MR imaging data, and literature.

| Segment | Cadaver (mm) | MR imaging data (mm) | Lang 1983 (mm) | Ko 2004 (mm) | Toossi 2021 (mm) | Mendez 2021 (mm) | Zhou 2010 (mm) | d'Avella 1979 (mm) | Frostell 2016 (mm) |
|---|---|---|---|---|---|---|---|---|---|
| L1 | 13.14 | 13.60 | 10.33 | 11.25 | 15.97 | 17.47 | 11.10 | 12.50 | 14.81 |
| L2 | 9.48 | 10.93 | 9.88 | 9.98 | 12.53 | 13.99 | 8.94 | 11.50 | 11.52 |
| L3 | 9.47 | 10.51 | 8.75 | 8.33 | 9.69 | 11.25 | 8.04 | 10.40 | 9.87 |
| L4 | 8.26 | 7.48 | 7.78 | 7.05 | 8.17 | 12.59 | 6.95 | 9.50 | 9.05 |
| L5 | 8.86 | 7.56 | 6.29 | 6.15 | 7.00 | 9.94 | 6.36 | 7.90 | 6.99 |
| S1 | 9.27 | 6.44 | 6.89 | 5.18 | 7.00 | 6.89 | 5.28 | 7.00 | 6.17 |

TABLE 5

Average measurements of white matter widths of selected thoracic, lumbar, and sacral segments from cadaver study, MR imaging data, and literature.

| Segment | Cadaver (mm) | MR imaging data (mm) | Frostell 2016 (mm) | Toossi 2021 (mm) | Mendez 2021 (mm) |
|---|---|---|---|---|---|
| T12 | 8.58 | 9.10 | 8.20 | | 8.22 |
| L1 | 8.49 | 9.49 | 8.60 | 8.79 | 8.06 |
| L2 | 8.72 | 9.65 | 9.10 | 8.97 | 8.16 |
| L3 | 9.81 | 9.85 | 9.40 | 9.16 | 8.76 |
| L4 | 9.74 | 9.93 | 9.30 | 9.49 | 8.04 |
| L5 | 8.67 | 9.61 | 8.80 | 8.74 | 6.75 |
| S1 | 6.92 | 8.49 | 8.40 | 7.17 | |
| S2 | 6.04 | 6.89 | 7.10 | | |

TABLE 6

Average measurements of rootlet distances of selected thoracic, lumbar, and sacral segments from cadaver study, MR imaging data, and literature.

| Segment | Cadaver (mm) | MR imaging data (mm) | Mendez 2021 (mm) | Mean (mm) |
|---|---|---|---|---|
| T12 | 6.10 | 5.50 | 5.96 | 5.90 |
| L1 | 6.27 | 5.60 | 5.62 | 6.09 |
| L2 | 5.93 | 5.56 | 5.46 | 5.87 |
| L3 | 5.66 | 5.40 | 5.79 | 5.80 |
| L4 | 5.57 | 5.00 | 5.57 | 5.63 |
| L5 | 5.30 | 4.16 | 4.10 | 4.95 |
| S1 | 4.34 | 3.10 | | 4.21 |
| S2 | 3.21 | 2.66 | | 3.18 |

Anatomical measurement data shown in Tables 4-6 indicate that segment lengths around and/or in the lumbar region decreases rostro-caudally. Furthermore, white matter width increases to its maximum at about L3-L4 (e.g., at lumbar enlargement) and then decreases, forming a taper or V-shape (e.g., at the conus medullaris). The rootlet distance follows a similar pattern as the white matter width. In some embodiments, the vertical inter-electrode distance of the electrodes of a lead for stimulating the lumbar region may decrease to follow the decreasing segment lengths. In some embodiments, the horizontal inter-electrode distance of the electrodes of a lead for stimulating the lumbar region may follow the decreasing rootlet distances. In such embodiments, the distribution of the electrodes in the lead paddle may resemble a taper or V-shape.

Figure 6:
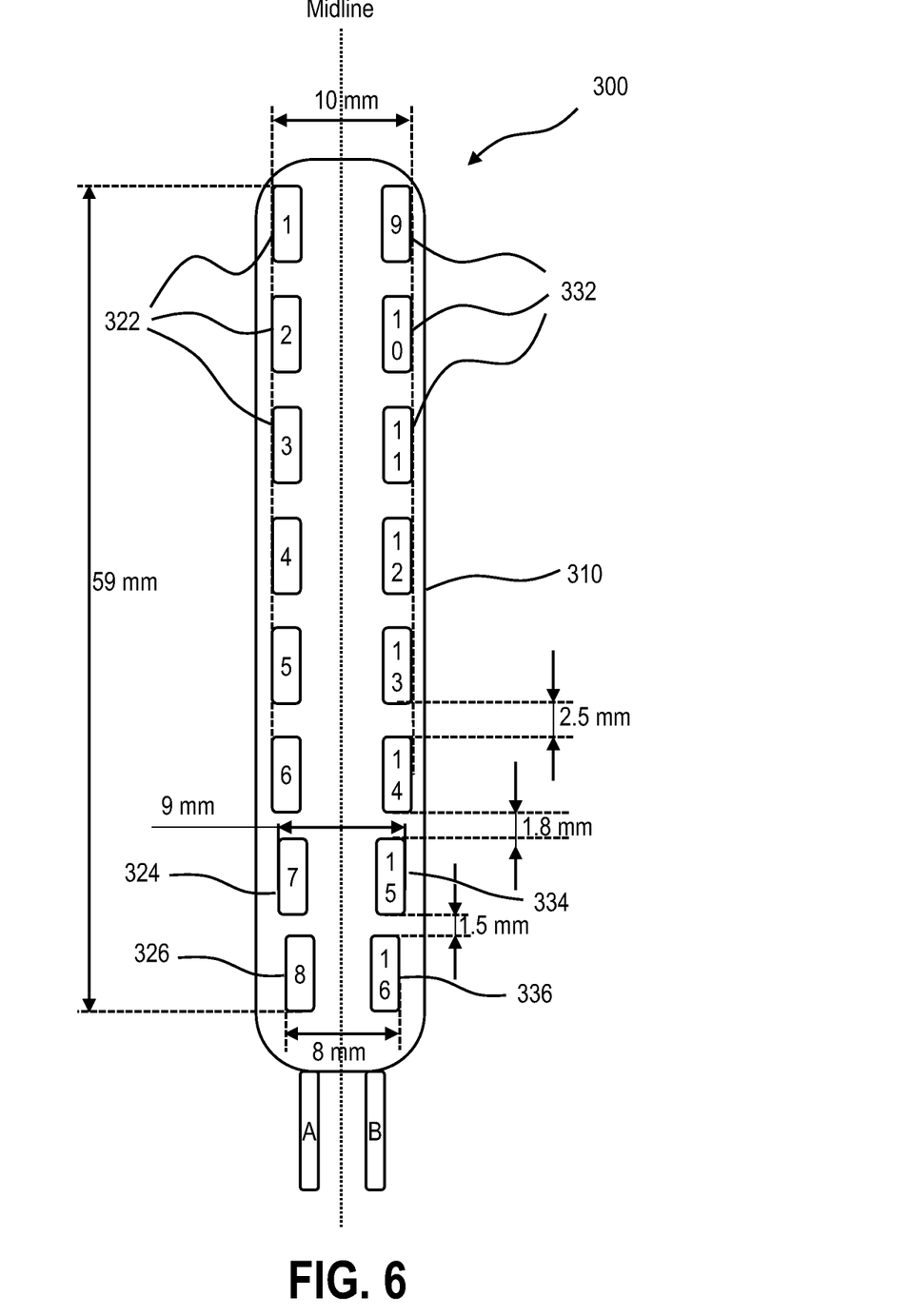
FIG. 6 depicts an exemplary lead for stimulating the lumbar spinal region, according to some embodiments of the present disclosure.
Figure 7:
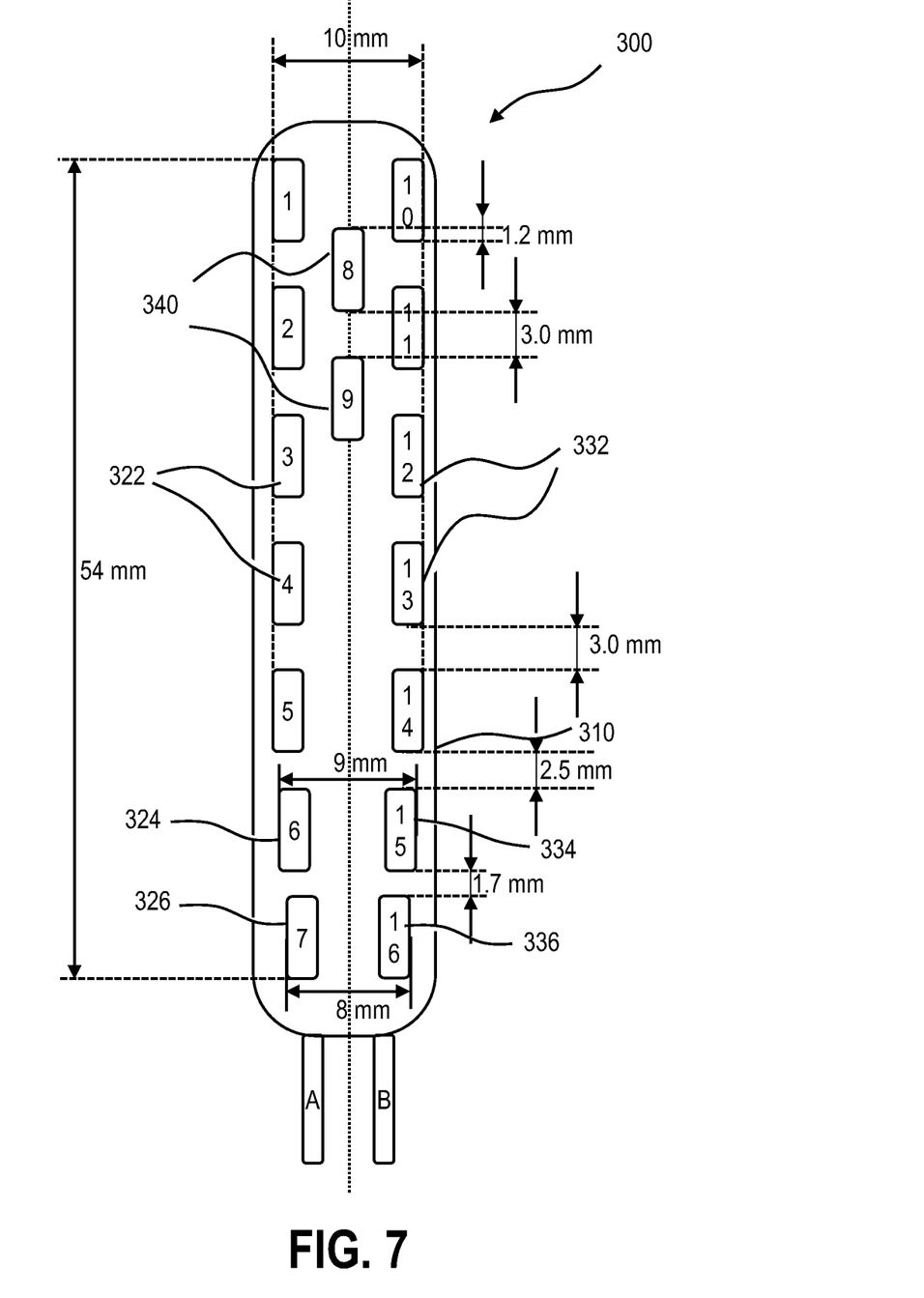
FIG. 7 depicts another exemplary lead for stimulating the lumbar spinal region, according to some embodiments of the present disclosure.

In some embodiments, based on the collected anatomical measurements and subsequent computational simulations, a lead for providing EES of selected segments in the lumbar region is provided. FIGS. 6-7 depicts exemplary leads 300 for stimulating the lumbar spinal region, according to some embodiments of the present disclosure. In some embodiments, lead 300 includes a paddle 310 and a plurality of electrodes 322, 324, and 326 of a first column and a plurality of electrodes 332, 334, and 336 of a second column.

For example, as shown in FIG. 6, in some embodiments, lead 300 includes an array of 16 electrodes symmetrically distributed about the midline of paddle 310. The 16 electrodes are numbered and distributed in two columns, each column comprising 8 electrodes. In some embodiments, the 16 electrodes are identical. In some embodiments, the electrodes have a rectangular shape. In some embodiments, the size of an electrode is about 5.4 mm by 2.04 mm.

In some embodiments, the electrodes of the first column or the second column are divided into one or more groups. Each group includes one or more electrodes. For example, in some embodiments, the electrodes of the first column are divided into a first group of electrodes 322 (e.g., electrodes 1-6), a second group of electrodes 324 (e.g., electrode 7), and a third group of electrodes 326 (e.g., electrode 8). Likewise, the electrodes of the second column are divided into a first group of electrodes 332 (e.g., electrodes 9-14), a second group of electrodes 334 (e.g., electrode 15), and a third group of electrodes 336 (e.g., electrode 16). In some embodiments, lead 300 includes a lead body A and a lead body B. Lead body A contain conductors contacts from the electrodes of the first column, e.g., electrodes 1-8, and lead body B contain conductors contacts from the electrodes of the second column, e.g., electrodes 9-16.

In some embodiments, the width of paddle 310 is equal to or less than about 13.0 mm. In some embodiments, the thickness of paddle 310 is equal to or less than about 2.5 mm. In some embodiments, as shown in FIG. 6, the distance between the top edge of electrode 1 and the bottom edge of electrode 8 along the longitudinal axis is from about 50.0 mm to about 71.0 mm, such as about 59.0 mm.

In some embodiments, the vertical inter-electrode distance of the first column of electrodes or the second column of electrodes decreases along the longitudinal axis of paddle 310. In some embodiments, the vertical inter-electrode distance of a first group of electrodes 322 of the first column or a first group of electrodes 332 of the second column (e.g., the distance between the bottom edge of electrode 15 and the top edge of electrode 16) is from about 1.0 mm to about 4.0 mm, such as about 2.5 mm. In some embodiments, the vertical inter-electrode distance between the last electrode of the first group and the first electrode of the second group of the first column or the second column (e.g., the distance between the bottom edge of electrode 14 and the top edge of electrode 15) is from about 1.3 mm to about 2.3 mm, such as about 1.8 mm. In some embodiments, the vertical inter-electrode distance between the last electrode of the second group and the first electrode of the third group of the first column or the second column (e.g., the distance between the bottom edge of electrode 15 and the top edge of electrode 16) is from about 1.0 mm to about 2.0 mm, such as about 1.5 mm.

In some embodiments, the horizontal inter-electrode distance of the first and second columns of electrodes decreases along the longitudinal axis of paddle 310. In some embodiments, as shown in FIG. 6, the horizontal inter-electrode distance between the first group of electrodes 322 of the first column and the first group of electrodes 332 of the second column (e.g., the distance between the left edge of electrode 1 and the right edge of an electrode 9) is from about 8.0 mm to about 12.0 mm, such as about 10.0 mm. In such instances, the center of an electrode of the first group, e.g., electrode 322 or electrode 332, is about 3.0 mm to about 5.0 mm, such as about 4 mm, away from the midline of paddle 310.

In some embodiments, the horizontal inter-electrode distance between the second group of electrodes 324 of the first column and the second group of electrodes 332 of the second column (e.g., the distance between the left edge of electrode 7 and the right edge of an electrode 15) is from about 7.0 mm to about 11.0 mm, such as about 9.0 mm. In such instances, the center of an electrode of the second group, e.g., electrode 324 or electrode 334, is about 2.5 mm to about 4.5 mm, such as about 3.5 mm, away from the midline of paddle 310.

In some embodiments, the horizontal inter-electrode distance between the third group of electrodes 326 of the first column and the third group of electrodes 336 of the second column (e.g., the distance between the left edge of electrode 8 and the right edge of an electrode 16) is from about 6.0 mm to about 10.0 mm, such as about 8.0 mm. In such instances, the center of an electrode of the second group, e.g., electrode 326 or electrode 336, is about 2.0 mm to about 4.0 mm, such as about 3 mm, away from the midline of paddle 310.

As described herein, the number of groups of electrodes of lead 300 and the number of electrodes in each group may change based on one or more anatomical landmarks of the spinal segments of interest and/or results of computational simulations. In some embodiments, the number of groups of electrodes of lead 300 and the number of electrodes in each group may change based on the total number and/or density of the electrodes in paddle 310. The grouping of electrodes and number of electrodes in each group described herein are exemplary only.

FIG. 7 depicts another exemplary lead 300 for stimulating the lumbar spinal region, according to some embodiments of the present disclosure. As shown in FIG. 7, in some embodiments, lead 300 includes a third column of electrodes 340. In some embodiments, the third column of electrodes 340 are distributed along the midline of paddle 310. For example, as shown in FIG. 7, lead 300 includes an array of 16 electrodes symmetrically distributed about the midline of paddle 310. The 16 electrodes are numbered and distributed in three columns, the first column comprising electrodes 17, the second column comprising electrodes 1016, and the third column comprising electrodes 89. As described herein, the number of electrodes in each column may change based on the desired number and/or density of electrodes on the lateral sides of paddle 310 for effective recruitment of the dorsal roots of the lumbar region.

Similar to the embodiment of FIG. 6, in some embodiments, the electrodes of the first column or the second column are divided into one or more groups. Each group includes one or more electrodes. For example, as shown in FIG. 7, the electrodes of the first column are divided into a first group of electrodes 322 (e.g., electrodes 1-5), a second group of electrodes 324 (e.g., electrode 6), and a third group of electrodes 326 (e.g., electrode 7). The electrodes of the second column are divided into a first group of electrodes 332 (e.g., electrodes 10-14), a second group of electrodes 334 (e.g., electrode 15), and a third group of electrodes 336 (e.g., electrode 16). Lead body A contain conductors contacts from electrodes 1-8, and lead body B contain conductors contacts from electrodes 9-16.

Because the number of electrodes in the first and second columns are reduced, the vertical inter-electrode distance between the electrodes may increase to cover the same length of a spinal region. For example, in some embodiments, the vertical inter-electrode distance of first group of electrodes 322 of the first column or first group of electrodes 332 of the second column (e.g., the distance between the bottom edge of electrode 13 and the top edge of electrode 14) is from about 2.5 mm to about 3.5 mm, such as about 3.0 mm. In some embodiments, the vertical inter-electrode distance between the last electrode of the first group and the first electrode of the second group of the first column or the second column (e.g., the distance between the bottom edge of electrode 14 and the top edge of electrode 15) is from about 2.0 mm to about 3.0 mm, such as about 2.5 mm. In some embodiments, the vertical inter-electrode distance between the last electrode of the second group and the first electrode of the third group of the first column or the second column (e.g., the distance between the bottom edge of electrode 15 and the top edge of electrode 16) is from about 1.2 mm to about 2.2 mm, such as about 1.7 mm.

In some embodiments, the third column of electrodes are located between selected electrodes of the first group of electrodes of the first and second columns. In some embodiments, the vertical inter-electrode distance of the third column of electrodes (e.g., the distance between the bottom edge of electrode 8 and the top edge of electrode 9) is from about 2.5 mm to about 3.5 mm, such as about 3.0 mm. In other embodiments, the third column of electrodes may be located between the second and/or third group of electrodes and the vertical inter-electrode distance of the third column of electrodes may be reduced.

Exemplary Lead for Stimulating the Sacral Spinal Region

Anatomical measurement data on the segments of interest L5-S4 along the spinal cord were collected from the cadaver study, MR imaging data, data from three patients participating the STIMO ("STImulation Movement Overground") clinical study, and/or literature references (see Tables 7). The literature references include Ko 2004; Frostell 2016; Mendez 2021; Lang 1983; Toossi 2021; Zhou 2010; d'Avella 1979; and Mamatha et al., Morphology of nerve rootlets and spinal segments in the lumbosacral region: An anatomical study. *Research Journal of Pharmaceutical, Biological and Chemical Sciences,* 7(1), 1848-1854 (2016). All of these references are incorporated herein by reference in their entireties.

TABLE 7

Average measurements of selected lumbar and sacral segment lengths from cadaver study, MR imaging data, STIMO clinical study, and literature.

| Segment | Cadaver (mm) | MR imaging data (mm) | STIMO (mm) | Lang 1983 (mm) | Ko 2004 (mm) | Toossi 2021 (mm) | Mendez 2021 (mm) | Zhou 2010 (mm) | d'Avella 1979 (mm) | Mamatha 2016 (mm) | Mean (mm) |
|---|---|---|---|---|---|---|---|---|---|---|---|
| L5 | 7.56 | 8.63 | 9.19 | 6.29 | 6.15 | 7.00 | 9.94 | 6.36 | 7.90 | 11.14 | 8.02 |
| S1 | 6.44 | 5.94 | 5.74 | 6.89 | 5.18 | 7.00 | 7.71 | 5.28 | 7.00 | 11.14 | 6.83 |
| S2 | 6.62 | 6.34 | 6.12 | 6.39 | 4.60 | 6.72 | 8.22 | 4.93 | 6.80 | 7.77 | 6.45 |
| S3 | 5.52 | 5.54 | 5.36 | 4.74 | 4.47 | 5.88 | 7.19 | 4.56 | 5.71 | 7.11 | 5.61 |
| S4 | 5.13 | 5.15 | 4.97 | 4.40 | 4.07 | 5.46 | 6.68 | 4.24 | 5.30 | 5.49 | 5.09 |
| L5-S3 | 26.14 | 26.46 | 26.40 | 24.31 | 20.39 | 26.60 | 33.06 | 21.13 | 27.41 | 37.17 | 26.91 |
| L5-S4 | 31.26 | 31.60 | 31.38 | 28.72 | 24.46 | 32.06 | 39.73 | 25.37 | 32.71 | 42.66 | 32.00 |
| L5 | 7.56 | 8.63 | 9.19 | 6.29 | 6.15 | 7.00 | 9.94 | 6.36 | 7.90 | 11.14 | 8.02 |

TABLE 8

Average measurements of white matter widths of selected lumbar and sacral segments from cadaver study and literature.

| Segment | Cadaver (mm) | Frostell 2016 (mm) |
|---|---|---|
| L5 | 8.67 | 8.80 |
| S1 | 6.92 | 8.40 |
| S2 | 6.04 | 7.10 |
| S3 | 5.30 | 6.30 |
| S4 | 4.61 | 5.50 |

Like the lumbar region, anatomical measurement data shown in Tables 7-8 indicate that segment lengths in the sacral region decreases rostro-caudally. Furthermore, white matter width and rootlet distance also decrease rostro-caudally, forming a taper or V-shape (e.g., at the conus medullaris). In some embodiments, the vertical inter-electrode distance of the electrodes of a lead for stimulating the sacral region may decrease to follow the decreasing segment lengths. In some embodiments, the horizontal inter-electrode distance of the electrodes of a lead for stimulating the sacral region may follow the decreasing white matter widths or rootlet distances. In such embodiments, the distribution of the electrodes in the lead paddle may resemble a taper or V-shape.

Figure 8:
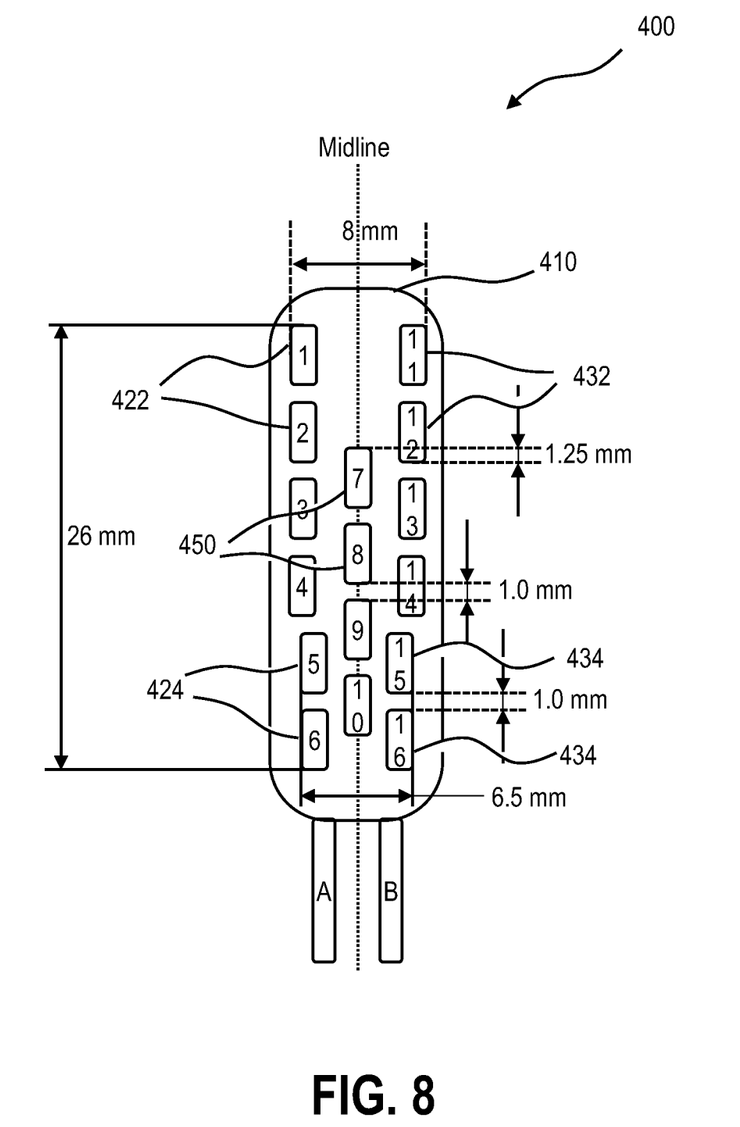
FIG. 8 depicts an exemplary lead for stimulating the sacral spinal region, according to some embodiments of the present disclosure.

In some embodiments, based on the collected anatomical measurements and subsequent computational simulations, a lead for providing EES of selected segments in the sacral region is provided. FIG. 8 depicts exemplary leads 400 for stimulating the sacral spinal region, according to some embodiments of the present disclosure. In some embodiments, lead 400 includes a paddle 410 and a plurality of electrodes distributed along in two or more columns.

For example, as shown in FIG. 8, in some embodiments, lead 400 includes an array of 16 electrodes symetrically distributed about the midline of paddle 310. The 16 electrodes are numbered and distributed in three columns, a first column comprising electrodes 1-7, a second column comprising electrodes 11-16, and a third column comprising electrodes 7-10. In some embodiments, the electrodes have a rectangular shape. In some embodiments, the size of an electrode is about 3.5 mm by 1.5 mm.

In some embodiments, the electrodes of the first column or the second column are divided into one or more groups. Each group includes one or more electrodes. For example, in some embodiments, the electrodes of the first column are divided into a first group of electrodes 422 (e.g., electrodes 1-4) and a second group of electrodes 424 (e.g., electrodes 5-6). Likewise, the electrodes of the second column are divided into a first group of electrodes 432 (e.g., electrodes 11-14) and a second group of electrodes 434 (e.g., electrodes 15-16). Lead body A contain conductors contacts from electrodes 1-8, and lead body B contain conductors contacts from electrodes 9-16.

In some embodiments, the width of paddle 410 is equal to or less than about 11 mm. In some embodiments, the thickness of paddle 410 is equal to or less than about 2.5 mm. In some embodiments, as shown in FIG. 8, the distance between the top edge of electrode 1 and the bottom edge of electrode 7 along the longitudinal axis is from about 23.0 mm to about 29.0 mm, such as about 54.0 mm.

In some embodiments, the vertical inter-electrode distance of the first column of electrodes or the second column of electrodes decreases along the longitudinal axis of paddle 410. In some embodiments, the vertical inter-electrode distance of the first column of electrodes or the second column of electrodes remains the same along the longitudinal axis of paddle 410. In some embodiments, the vertical inter-electrode distance of a first group of electrodes 422 of the first column or a first group of electrodes 432 of the second column (e.g., the distance between the bottom edge of electrode 3 and the top edge of electrode 4) is from about 0.5 mm to about 1.5 mm, such as about 1.0 mm. In some embodiments, the vertical inter-electrode distance between the last electrode of the first group and the first electrode of the second group of the first column or the second column (e.g., the distance between the bottom edge of electrode 4 and the top edge of electrode 5) is from about 0.5 mm to about 1.5 mm, such as about 1.0 mm.

In some embodiments, the horizontal inter-electrode distance of the first and second columns of electrodes decreases along the longitudinal axis of paddle 410. In some embodiments, as shown in FIG. 8, the horizontal inter-electrode distance between the first group of electrodes 422 of the first column and the first group of electrodes 432 of the second column (e.g., the distance between the left edge of electrode 1 and the right edge of an electrode 11) is from about 7.0 mm to about 9.0 mm, such as about 8.0 mm. In such instances, the center of an electrode of the first group, e.g., electrode 322 or electrode 332, is about 2.75 mm to about 3.75 mm, such as about 3.25 mm, away from the midline of paddle 310.

In some embodiments, the horizontal inter-electrode distance between the second group of electrodes 424 of the first column and the second group of electrodes 432 of the second column (e.g., the distance between the left edge of electrode 6 and the right edge of an electrode 16) is from about 6.0 mm to about 7.0 mm, such as about 6.5 mm. In such instances, the center of an electrode of the second group, e.g., electrode 424 or electrode 434, is about 2.25 mm to about 2.75 mm, such as about 2.5 mm, away from the midline of paddle 310.

In some embodiments, the third column of electrodes of lead 400 are located between electrodes of the first and/or second group of electrodes of the first and second columns. In some embodiments, the vertical inter-electrode distance of the third column of electrodes (e.g., the distance between the bottom edge of electrode 8 and the top edge of electrode 9) is from about 0.5 mm to about 1.5 mm, such as about 1.0 mm.

In some embodiments, a system for EES is provided. In some embodiments, the system includes at least one lead to be implanted at a stimulation site on top of the dura matter of the spinal cord tissue of the patient. In some embodiments, after implantation, the electrodes of the lead are positioned above the locations where dorsal roots or dorsal rootlets enter the spinal cord, i.e., at the dorsal root entry zone. In some embodiments, the system includes a pulse generator electrically coupled to the electrodes of the lead via the lead bodies. In some embodiments, the pulse generator may be implanted at or located remotely from the stimulation site. In some embodiments, the pulse generator is a portable device to be held, carried, and/or programmed by the patient or a clinical professional attending the patient. In some embodiments, the pulse generator may generate electrical stimulation pulses in accordance with stimulation parameters selected by the patient or the clinical professional. In some embodiments, the pulse generator may be programmed remotely using an electronic device, such as a mobile phone, a tablet, or a computer with a programming software package installed thereon.

The foregoing descriptions have been presented for purposes of illustration. They are not exhaustive and are not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

It should be noted that, the relational terms herein such as "first" and "second" are used only to differentiate an entity or operation from another entity or operation, and do not require or imply any actual relationship or sequence between these entities or operations. Moreover, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the terms "and/or" and "or" encompass all possible combinations, except where infeasible. For example, if it is stated that a database may include A or B, then, unless specifically stated otherwise or infeasible, the database may include A, or B, or A and B. As a second example, if it is stated that a database may include A, B, or C, then, unless specifically stated otherwise or infeasible, the database may include A, or B, or C, or A and B, or A and C, or B and C, or A and B and C.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only, with a true scope and spirit of the invention being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

The invention claimed is:

1. A lead for spinal cord simulation, the lead comprising:
    a paddle having a distal end and a proximal end along a midline of the paddle; and
    an electrode array distributed in the paddle, the electrode array comprising a first column of electrodes and a second column of electrodes;
    wherein:
        the first column of electrodes and the second column of electrodes are symmetric about the midline of the paddle;
        the first column of electrodes and the second column of electrodes each comprises a plurality of electrodes; and
        a vertical inter-electrode distance between the plurality of electrodes within the first or second column of electrodes decreases from the distal end to the proximal end.

2. The lead of claim 1, further comprising a third column of electrodes distributed along the midline of the paddle.

3. The lead of claim 1, further comprising two lead bodies configured to electrically couple the electrodes of the electrode array to a pulse generator.

4. A method of providing therapy for neurological disorders, the method comprising:

providing epidural electrical stimulation of the dura mater of at least one dorsal root of one or more spinal segments using a lead, the lead comprising a paddle and an electrode array distributed in the paddle, the electrode array comprising a first column of electrodes and a second column of electrodes, the paddle having a distal end and a proximal end along a midline of the paddle;

wherein:

the first column of electrodes and the second column of electrodes are symmetric about the midline of the paddle;

the first column of electrodes and the second column of electrodes each comprises a plurality of electrodes; and a vertical inter-electrode distance between the plurality of electrodes within the first or second column of electrodes decreases from the distal end to the proximal end.

5. The method of claim 4, wherein the one or more spinal segments include at least one lumbar segment.

6. The method of claim 4, wherein the one or more spinal segments include at least one sacral segment.

7. The method of claim 4, further comprising placing the lead on top of the dura matter of the spinal cord of the patient such that the electrodes of the first column and the second column are positioned at the dorsal root entry zone of the one or more spinal segments.

8. The method of claim 4, further comprising treating a neuromotor disorder or an autonomic dysfunction.

9. The method of claim 4, wherein the lead further comprises a third column of electrodes distributed along the midline of the paddle.

10. A system for spinal cord stimulation, the system comprising:

a pulse generator; and a lead comprising a paddle and an electrode array distributed in the paddle, the electrode array comprising a first column of electrodes and a second column of electrodes, the paddle having a distal end and a proximal end along a midline of the paddle;

wherein:

the first column of electrodes and the second column of electrodes are symmetric about the midline of the paddle;

the first column of electrodes and the second column of electrodes each comprises a plurality of electrodes; and a vertical inter-electrode distance between the plurality of electrodes within the first or second column of electrodes decreases from the distal end to the proximal end.

11. The system of claim 10, further comprising a third column of electrodes distributed along the midline of the paddle.

* * * * *